(12) United States Patent
Frick et al.

(10) Patent No.: US 6,569,835 B2
(45) Date of Patent: *May 27, 2003

(54) COMBINATIONS WITH STATIN AND ARYL-SUBSTITUTED PROPANOLAMINE DERIVATIVES, THEIR PREPARATION PHARMACEUTICALS COMPRISING THEM, AND THEIR USE

(75) Inventors: Wendelin Frick, Hünstetten-Beuerbach (DE); Reinhard Kirsch, Braunschweig (DE); Heiner Glombik, Hofheim (DE); Werner Kramer, Mainz-Laubenheim (DE); Hans-Ludwig Schäfer, Hochheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/985,149

(22) Filed: Nov. 1, 2001

(65) Prior Publication Data

US 2002/0177610 A1 Nov. 28, 2002

Related U.S. Application Data

(60) Continuation of application No. 09/833,676, filed on Apr. 13, 2001, which is a division of application No. 09/410,084, filed on Oct. 1, 1999, now Pat. No. 6,245,744.

(30) Foreign Application Priority Data

Oct. 2, 1998 (DE) .......................... 198 45 405

(51) Int. Cl.⁷ .............................................. A61K 31/70
(52) U.S. Cl. ............................ 514/25; 514/53; 514/54; 514/61
(58) Field of Search .................. 514/25, 53, 54, 514/61

(56) References Cited

U.S. PATENT DOCUMENTS 5,571,816 A    11/1996   Kampe et al. ............... 514/275
5,874,451 A    2/1999    Glombik et al. ............ 514/357
6,391,915 B2 *  5/2002    Tanaguchi et al. .......... 514/510

FOREIGN PATENT DOCUMENTS

| EP | 0 557 879 A1 | 9/1993 |
| EP | 0 869 121 A1 | 10/1998 |
| WO | WO 93/16055 | 8/1993 |

OTHER PUBLICATIONS

English Abstracts, Derwent No. 93–274361/199335.

English Abstracts, Derwent No. 98–508454.

International Search Report, dated Dec. 21, 1999.

* cited by examiner

*Primary Examiner*—Kathleen K. Fonda
(74) *Attorney, Agent, or Firm*—Finnegan, Henderson, Farabow, Garrett, & Dunner, L.L.P.

(57) ABSTRACT

Substituted propanolamine derivatives, their pharmaceutically tolerated salts and physiologically functional derivatives thereof are described. Also described are compounds of formula I

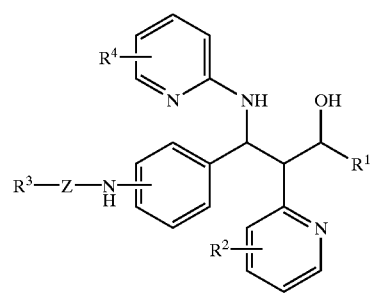

in which the radicals have the abovementioned meanings, and their physiologically tolerated salts, physiologically functional derivatives and processes for their preparation. The compounds are suitable as, for example, hypolipidemics.

22 Claims, 1 Drawing Sheet

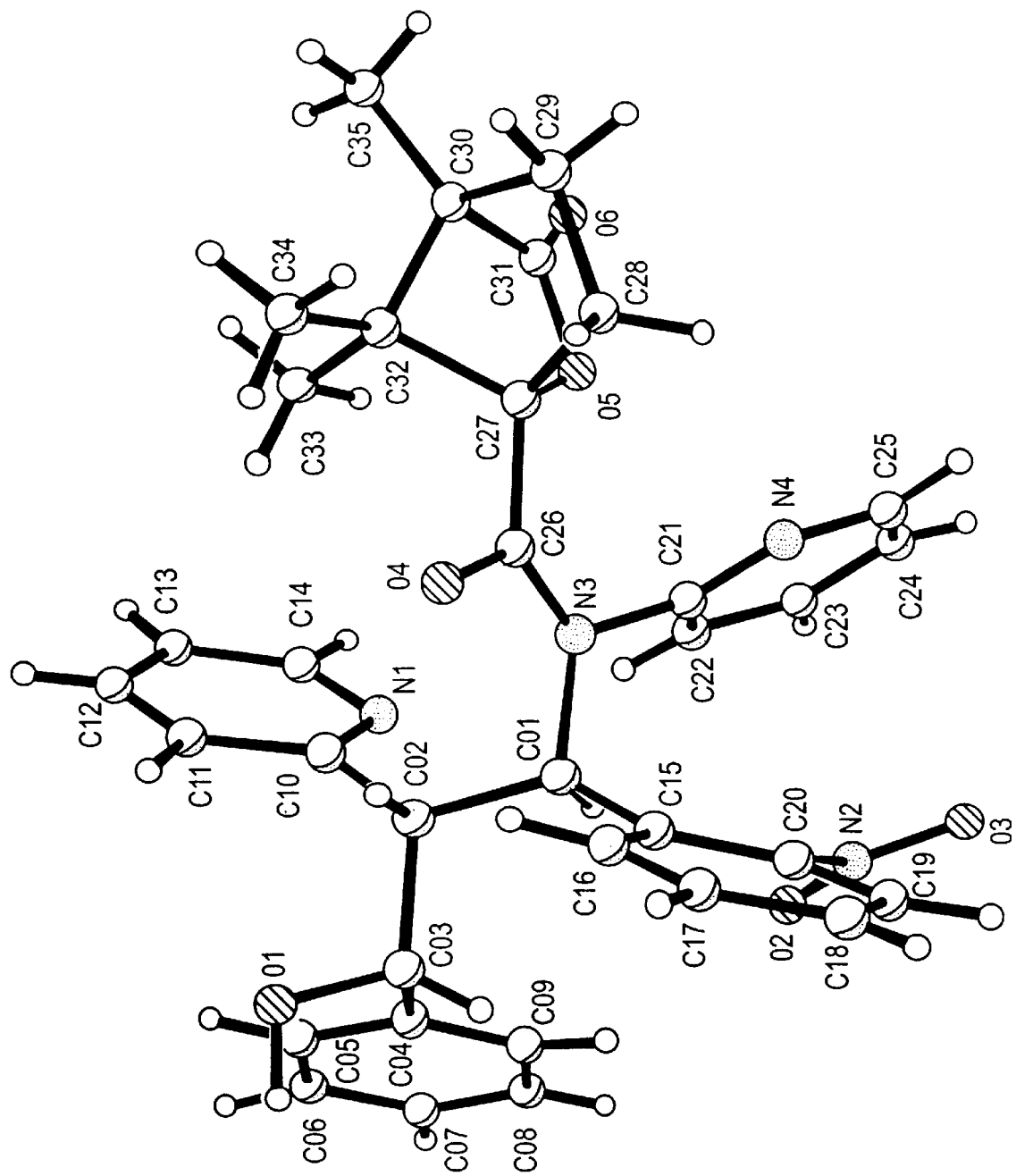

COMBINATIONS WITH STATIN AND ARYL-SUBSTITUTED PROPANOLAMINE DERIVATIVES, THEIR PREPARATION PHARMACEUTICALS COMPRISING THEM, AND THEIR USE

This is a continuation of Ser. No. 09/833,676 filed, Apr. 13, 2001, which is a division of application Ser. No. 09/410,084, filed Oct. 1, 1999, now U.S. Pat. No. 6,245,744, all of which are incorporated herein by reference.

The invention relates to substituted propanolamine derivatives and to their acid addition salts.

Several classes of active substances for the treatment of obesity and disorders of lipid metabolism have already been described:

polymeric adsorbers such as, for example, cholestyramine, benzothiazepines (WO 93/16055), bile acid dimers and conjugates (EP 0 489 423) and 4-amino-2-ureidopyrimidine-5-carboxamides (EP 0 557 879).

The invention was based on the object of providing further compounds which have a therapeutically exploitable hypolipidemic effect.

The invention therefore relates to propanolamine derivatives of formula I

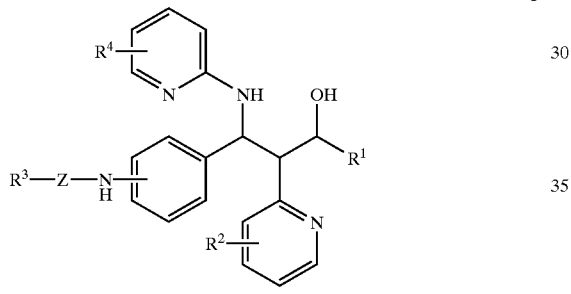

I in which $R^1$ is phenyl, or heteroaryl, which is unsubstituted or optionally substituted by one to three independent radicals, it being possible for the aromatic or heteroaromatic ring to be mono- to trisubstituted by fluorine, chlorine, bromine, iodine, —OH, —$CF_3$, —$NO_2$, —CN, —($C_1$-$C_8$)-alkoxy, —($C_1$-$C_8$)-alkyl, —$NH_2$, —NH—$R^9$, —N($R^9$)$R^{10}$, —CHO, —COOH, —$COOR^{11}$, —(C=O)—$R^{12}$, —($C_1$-$C_6$)-alkyl-OH, —($C_1$-$C_6$)-alkyl(—OH)-phenyl, —($C_1$-$C_6$)-alkyl-$CF_3$, —($C_1$-$C_6$)-alkyl-$NO_2$, —($C_1$-$C_6$)-alkyl-CN, —($C_1$-$C_6$)-alkyl-$NH_2$, —($C_1$-$C_6$)-alkyl-NH—$R^9$, —($C_1$-$C_6$)-alkyl-N($R^9$)$R^{10}$, —($C_1$-$C_6$)-alkyl-CHO, —($C_1$-$C_6$)-alkyl-COOH, —($C_1$-$C_6$)-alkyl-COOR , —($C_1$-$C_6$)-alkyl-(C=O)—$R^{12}$, —O—($C_1$-$C_6$)-alkyl-OH, —O—($C_1$-$C_6$)-alkyl-$CF_3$, —O—($C_1$-$C_6$)-alkyl-$NO_2$, —O—($C_1$-$C_6$)-alkyl-CN, —O—($C_1$-$C_6$)-alkyl-$NH_2$, —O—($C_1$-$C_6$)-alkyl-NH—$R^9$, —O—($C_1$-$C_6$)-alkyl-N($R^9$)$R^{10}$, —O—($C_1$-$C_6$)-alkyl-CHO, —O—($C_1$-$C_6$)-alkyl-COOH, —O—($C_1$-$C_6$)-alkyl-$COOR^{11}$, —O—($C_1$-$C_6$)-alkyl-(C=O)—$R^{12}$, —N—$SO_3$H, —$SO_2$—$CH_3$, —O—($C_1$-$C_6$)-alkyl-O—($C_1$-$C_6$)-alkyl-phenyl, ($C_1$-$C_6$)-alkylthio, or pyridyl, it being possible for one or more hydrogen(s) in the alkyl radicals to be replaced by fluorine and it being possible for phenyl and pyridyl, in turn, to be monosubstituted by methyl, methoxy or halogen;

$R^2$ is H, —OH, —$CH_2$OH, —OMe, —CHO, or —$NH_2$;

$R^3$ is a sugar residue, disugar residue, trisugar residue, tetrasugar residue, it being possible for the sugar residue, disugar residue, trisugar residue or tetrasugar residue to be optionally mono- or polysubstituted by one of the sugar protective groups, HO—$SO_2$—, or (HO)$_2$—PO—;

$R^4$ is H, methyl, F, or —OMe;

$R^9$ to $R^{12}$ each independently of one another is H or —($C_1$-$C_8$)-alkyl;

Z is —NH—($C_0$-$C_{16}$)-alkyl-C=O—, —O—($C_0$-$C_{16}$)-alkyl-C=O—, —(C=O)$_m$—($C_1$-$C_{16}$)-alkyl-(C=O)$_n$, amino acid residue, diamino acid residue, it being possible for the amino acid residue or diamino acid residue optionally to be mono- or polysubstituted by an amino acid protective group, or a covalent bond;

n is 0 or 1;

m is 0 or 1;

and their pharmaceutically tolerated salts and physiologically functional derivatives.

Preferred compounds of formula I are those in which one or more radical(s) has, or have, the following meaning:

$R^1$ is phenyl, pyridyl, thienyl, furyl, pyrimidyl, indolyl, thiazolyl, imidazolyl, coumarinyl, phthaliminyl, quinoyl, piperazinyl, tetrazolyl, triazolyl, oxazolyl, isoxazolyl, isothiazolyl or their benzo-fused derivatives, it being possible for the aromatic or heteroaromatic ring to be mono- to trisubstituted by fluorine, chlorine, bromine, iodine, —OH, —$CF_3$, —$NO_2$, —CN, —($C_1$-$C_8$)-alkoxy, —($C_1$-$C_8$)-alkyl, —$NH_2$, —NH—$R^9$, —N($R^9$)$R^{10}$, —CHO, —COOH, —$COOR^{11}$, —(C=O)—$R^{12}$, —($C_1$-$C_6$)-alkyl-OH, —($C_1$-$C_6$)-alkyl(—OH)-phenyl, —($C_1$-$C_6$)-alkyl-$CF_3$, —($C_1$-$C_6$)-alkyl-$NO_2$, ($C_1$-$C_6$)-alkyl-CN, —($C_1$-$C_6$)-alkyl-$NH_2$, —($C_1$-$C_6$)-alkyl-NH—$R^9$, —($C_1$-$C_6$)-alkyl-N($R^9$)$R^{10}$, —($C_1$-$C_6$)-alkyl-CHO, —($C_1$-$C_6$)-alkyl-COOH, —($C_1$-$C_6$)-alkyl-$COOR^{11}$, —($C_1$-$C_6$)-alkyl-(C=O)—$R^{12}$, —O—($C_1$-$C_6$)-alkyl-OH, —O—($C_1$-$C_6$)-alkyl-$CF_3$, —O—($C_1$-$C_6$)-alkyl-$NO_2$, —O—($C_1$-$C_6$)-alkyl-CN, —O—($C_1$-$C_6$)-alkyl-$NH_2$, —O—($C_1$-$C_6$)-alkyl-NH—$R^9$, —O—($C_1$-$C_6$)-alkyl-N($R_9$)$R^{10}$, —O—($C_1$-$C_6$)-alkyl-CHO, —O—($C_1$-$C_6$)-alkyl-COOH, —O—($C_1$-$C_6$)-alkyl-$COOR^{11}$, —O—($C_1$-$C_6$)-alkyl-(C=O)—$R^{12}$, —N—$SO_3$H, —$SO_2$—$CH_3$, —O—($C_1$-$C_6$)-alkyl-O—($C_1$-$C_6$)-alkyl-phenyl, —($C_1$-$C_6$)-alkylthio, pyridyl, it being possible for one or more hydrogen(s) in the alkyl radicals to be replaced by fluorine and it being possible for phenyl and pyridyl, in turn, to be monosubstituted by methyl, methoxy or halogen;

$R^2$ is H, —OH, —$CH_2$OH, —OMe, —CHO, or —$NH_2$;

$R^3$ is a sugar residue, disugar residue, trisugar residue, tetrasugar residue, it being possible for the sugar residue, disugar residue, trisugar residue or tetrasugar residue to be optionally mono- or polysubstituted by a sugar protective group, HO—$SO_2$—, or (HO)$_2$—PO—;

$R^4$ is H, methyl, F, or —OMe;

$R^9$ to $R^{12}$ each independently of one another is H, or —($C_1$-$C_8$)-alkyl;

Z is —NH—($C_0$-$C_{16}$)-alkyl-C=O—, —O—($C_0$-$C_{16}$)-alkyl-C=O—, —(C=O)$_m$—($C_1$-$C_{16}$)-alkyl-(C=O)$_n$, an amino acid residue, a diamino acid residue, it being possible for the amino acid residue or the diamino acid residue optionally to be mono- or polysubstituted by an amino acid protective group, or a covalent bond;

n is 0 or 1;
m is 0 or 1;
and their pharmaceutically tolerated salts and physiologically functional derivatives.

Especially preferred compounds of formula I are those in which one or more radical(s) has, or have, the following meaning:

$R^1$ is phenyl, pyridyl, thienyl, furyl, pyrimidyl, indolyl, thiazolyl, imidazolyl, coumarinyl, phthaliminyl, quinoyl, piperazinyl, tetrazolyl, triazolyl, oxazolyl, isoxazolyl, isthiazolyl, it being possible for the aromatic or heteroaromatic ring to be mono- or disubstituted by fluorine, chlorine, bromine, iodine, —OH, —$CF_3$, —$NO_2$, —CN, —($C_1$-$C_8$)-alkoxy, —($C_1$-$C_8$)-alkyl, —($C_3$-$C_6$)-cycloalkyl, —$NH_2$, —CHO, —COOH, or $OCF_3$;

$R^2$ is H, —OH, —$CH_2OH$, —OMe, CHO, or —$NH_2$;

$R^3$ is a sugar residue, a disugar residue, the sugar residue or disugar residue optionally being mono- or polysubstituted by one of the sugar protective groups, HO—$SO_2$—, or $(HO)_2$—PO—;

$R^4$ is H, methyl, F, or —OMe;

Z is —NH—($C_0$-$C_{16}$)-alkyl-C=O—, —O—($C_0$-$C_{16}$)-alkyl-C=O—, —(C=O)$_m$—($C_1$-$C_{16}$)-alkyl-(C=O)$_n$, or a covalent bond;

n is 0 or 1;
m is 0 or 1;
and their physiologically tolerated acid addition salts.

Very especially preferred compounds of formula I are those in which one or more radical(s) has, or have, the following meaning:

$R^1$ is phenyl, thiazolyl, oxazolyl, isoxazolyl, it being possible for the aromatic or heteroaromatic ring to be mono- to disubstituted by fluorine, chlorine, bromine, or —($C_1$-$C_8$)-alkyl;

$R^2$ is H, —OH, —$CH_2OH$, —OMe, —CHO, or —$NH_2$;

$R^3$ is

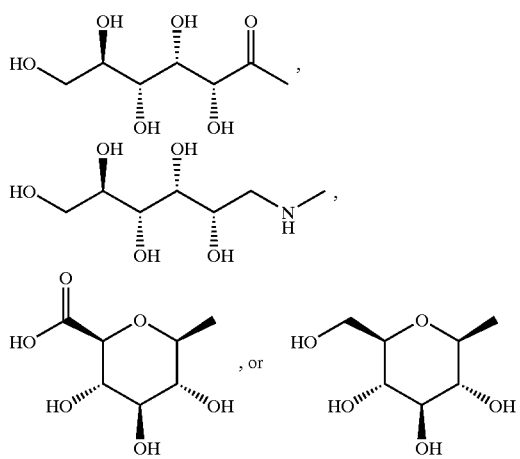

the sugar residue optionally being mono- or polysubstituted by one of the sugar protective groups, or HO—$SO_2$—;

$R^4$ is H, methyl, F, or —OMe;

Z is —NH—($C_6$-$C_{12}$)-alkyl-C=O—, —O—($C_6$-$C_{12}$)-alkyl-C=O—, or —(C=O)$_m$—($C_6$-$C_{12}$)-alkyl-(C=O)$_n$;

n is 0 or 1;
m is 0 or 1;
and their physiologically tolerated acid addition salts.

In the abovementioned heteroaryl groups, examples of suitable heteroatoms are O, S, and N.

Unless otherwise defined, heteroaromatic rings have 1–15 carbon atoms and 1–6 heteroatoms, preferably 1–5 carbon atoms and 1–2 heteroatoms.

Examples of the heteroaryl groups mentioned in the above definitions are thiophene, furan, pyridine, pyrimidine, indole, quinoline, oxazole, isoxazole, thiazole, or isothiazole.

The term alkyl is to be understood to mean straight-chain or branched hydrocarbon chains.

Sugar residues are to be understood to mean compounds derived from aldoses and ketoses having 3 to 7 carbon atoms, which can belong to the D- or L-series; they also include amino sugars, sugar alcohols or sugar acids. Examples which may be mentioned are glucose, mannose, fructose, galactose, ribose, erythrose, glycerinaldehyde, sedoheptulose, glucosamine, galactosamine, glucuronic acid, galacturonic acid, gluconic acid, galactonic acid, mannonic acid, glucamine, 3-amino-1,2-propanediol, glucaric acid and galactaric acid.

Disugars are to be understood as meaning saccharides which are composed of two sugar units. Di-, tri-, or tetrasaccharides are the result of an acetal-like linkage of 2 or more sugars. The linkages may occur in the α- or β-form. Examples which may be mentioned are lactose, maltose and cellobiose.

If the sugar is substituted, then the substitution is preferably on the hydrogen atom of an OH group of the sugar.

The following protective groups are essentially suitable for the hydroxyl groups of the sugars: benzyl, acetyl, benzoyl, pivaloyl, trityl, tert-butyldimethylsilyl, benzylidene, cyclohexylidene or isopropylidene protective groups.

The term amino acids or amino acid residues is to be understood as meaning the stereoisomeric forms, i.e., the D- or L-forms, of any of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| tryptophan | methionine | valine |
| tyrosine | asparagine | |

| | |
|---|---|
| 2-aminoadipic acid | 2-aminoisobutyric acid |
| 3-aminoadipic acid | 3-aminoisobutyric acid |
| beta-alanine | 2-aminopimelic acid |
| 2-aminobutyric acid | 2,4-diaminobutyric acid |
| 4-aminobutyric acid | desmosine |
| piperidinic acid | 2,2-diaminopimelic acid |
| 6-aminocaproic acid | 2,3-diaminopropionic acid |
| 2-aminoheptanoic acid | N-ethylglycine |
| 2-(2-thienyl)glycine | 3-(2-thienyl)alanine |
| penicillamine | N-methylglycine |
| N-ethylasparagine | N-methylisoleucine |
| hydroxylysine | 6-N-methyllysine |
| allo-hydroxylysine | N-methylvaline |
| 3-hydroxyproline | norvaline |
| 4-hydroxyproline | norleucine |
| isodesmosine | ornithine |
| allo-isoleucine | 11-aminoundecanoic acid |

The term amino-protective groups is to be understood as meaning suitable groups with which the functional groups of the side chains of the amino acid residues are protected (see, for example, T. W. Greene, P. G. M. Wuts, *Protective Groups in Organic Synthesis*, 2nd Edition, John Wiley and Sons, New York 1991). The following were typically used:

t-butyloxy-carbonyl (BOC), 9-fluorenylmethoxy-carbonyl (Fmoc), benzyloxy-carbonyl (Z), 2-(3,5-dimethoxyphenyl) prop-2-yloxycarbonyl (Ddz), methyl, t-butyl, trityl, S-t-butyl.

Pharmaceutically tolerated salts are especially suitable for medicinal applications owing to the fact that their solubility in water is better than the original compounds, or basic compounds. These salts must have a pharmaceutically tolerated anion or cation. Suitable pharmaceutically tolerated acid addition salts of the compounds according to the invention are salts of inorganic acids such as hydrochloric acid, hydrobromic acid, phosphoric acid, metaphosphoric acid, nitric acid, sulfonic acid and sulfuric acid, and of organic acids such as, for example, acetic acid, benzenesulfonic acid, benzoic acid, citric acid, ethanesulfonic acid, fumaric acid, gluconic acid, glycolic acid, isothionic acid, lactic acid, lactobionic acid, maleic acid, malic acid, methanesulfonic acid, succinic acid, p-toluene-sulfonic acid, tartaric acid and trifluoroacetic acid. The chloride salt is especially preferable for medicinal purposes. Suitable pharmaceutically tolerated basic salts are ammonium salts, alkali metal salts (such as sodium and potassium salts) and alkaline earth metal salts (such as magnesium and calcium salts).

Salts with an anion which is not pharmaceutically tolerated also come within the scope of the invention as useful intermediates for the preparation or purification of pharmaceutically tolerated salts and/or for the use in nontherapeutic applications, for example, in vitro applications.

The term "physiologically functional derivative" used herein designates any physiologically tolerated derivative of a compound of formula I according to the invention, for example an ester, which, upon administration to a mammal, such as, for example, humans, is capable (directly or indirectly) of forming a compound of formula I or an active metabolite thereof.

The physiologically functional derivatives also include prodrugs of the compounds according to the invention. Such prodrugs can be metabolized in vivo to give a compound according to the invention. These prodrugs may be active themselves or not.

The compounds according to the invention may also exist in various polymorphous forms, for example as amorphous and crystalline polymorphous forms. All polymorphous forms of the compounds according to the invention come within the scope of the invention and are a further aspect of the invention.

All references to "compound(s) of formula (I)" hereinbelow refer to a compound, or compounds, of formula (I) as described hereinabove and to their salts, solvates and physiologically functional derivatives as described herein.

The quantity of a compound of formula (I) required for the achievement of the desired biological effect depends on a series of factors, for example, the specific compound chosen, the desired use, the route of administration and the clinical condition of the patient. In general, the daily dose is from 0.1 mg to 100 mg (typically from 0.1 mg to 50 mg) per day per kilogram of body weight, for example 0.1–10 mg/kg/day. Tablets or capsules may contain, for example, 0.01 to 100 mg, typically 0.02 to 50 mg. In the case of pharmaceutically tolerated salts, the above weights relate to the weight of the aminopropanol ion derived from the salt. The compounds of formula (I) themselves can be used for prophylaxis or therapy of the abovementioned conditions in the form of a compound, but they are preferably present together with a tolerated excipient in the form of a pharmaceutical composition. Naturally, the excipient must be tolerated in the sense that it is compatible with the other components of the composition and is not harmful to the patient. The excipient can be a solid or a liquid or both and is preferably formulated together with the compound as a unit dose, for example a tablet which may contain 0.05% to 95% by weight of the active substance. Other pharmaceutically active substances may also be present, including other compounds of formula (I). The pharmaceutical compositions according to the invention can be prepared by one of the known pharmaceutical methods, which consist essentially in mixing the components with pharmacologically tolerated excipients and/or auxiliaries.

Pharmaceutical compositions according to the invention are those which are suitable for oral and peroral (for example sublingual) administration, even though the most suitable route of administration depends in each individual case on the nature and severity of the condition to be treated and on the nature of the compound used in each case. Sugar-coated formulations and sugar-coated slow-release formulations also fall within the scope of the invention. Acid-resistant and enteric formulations are preferred. Suitable enteric coatings encompass cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can exist in separate units, for example capsules, wafers, lozenges or tablets, each of which contains a specific quantity of the compound of formula (I); in the form of powder or granules; in the form of a solution or suspension, in an aqueous or nonaqueous fluid; or as an oil-in-water or water-in-oil emulsion. As has already been mentioned, these compositions are prepared by any suitable pharmaceutical method which encompasses a step in which the active substance and the excipient (which may consist of one or more additional components) are brought into contact with each other. In general, the compositions are prepared by uniformly and homogeneously mixing the active substance with a liquid and/or finely divided solid excipient, whereupon the product can be shaped, if so required. For example, a tablet can be prepared by compressing or shaping a powder or granule of the compound, if appropriate together with one or more additional components. Compressed tablets can be prepared by tableting the compound in free-flowing form, such as, for example, a powder or granules, if appropriate as a mixture with a binder, glidant, inert diluent and/or one (or more) surfactant/dispersant, in a suitable machine. Shaped tablets can be prepared by shaping the pulverulent compound with an inert liquid diluent, in a suitable machine.

Pharmaceutical compositions which are suitable for peroral (sublingual) administration encompass lozenges which comprise a compound of formula (I) together with a flavoring, usually sucrose and gum arabic or tragacanth, and pastilles, which comprise the compound in an inert base such as gelatin and glycerol or sucrose and gum arabic.

The invention furthermore also relates to isomer mixtures of formula I and to the pure diastereomers of formula I.

The invention furthermore relates to processes for the preparation of propanolamine derivatives of formula I.

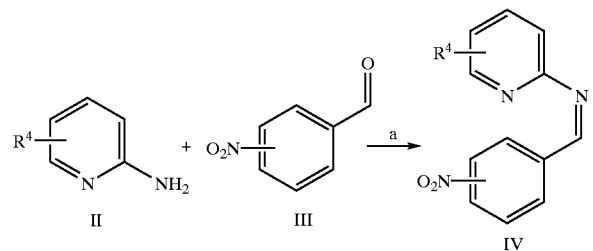

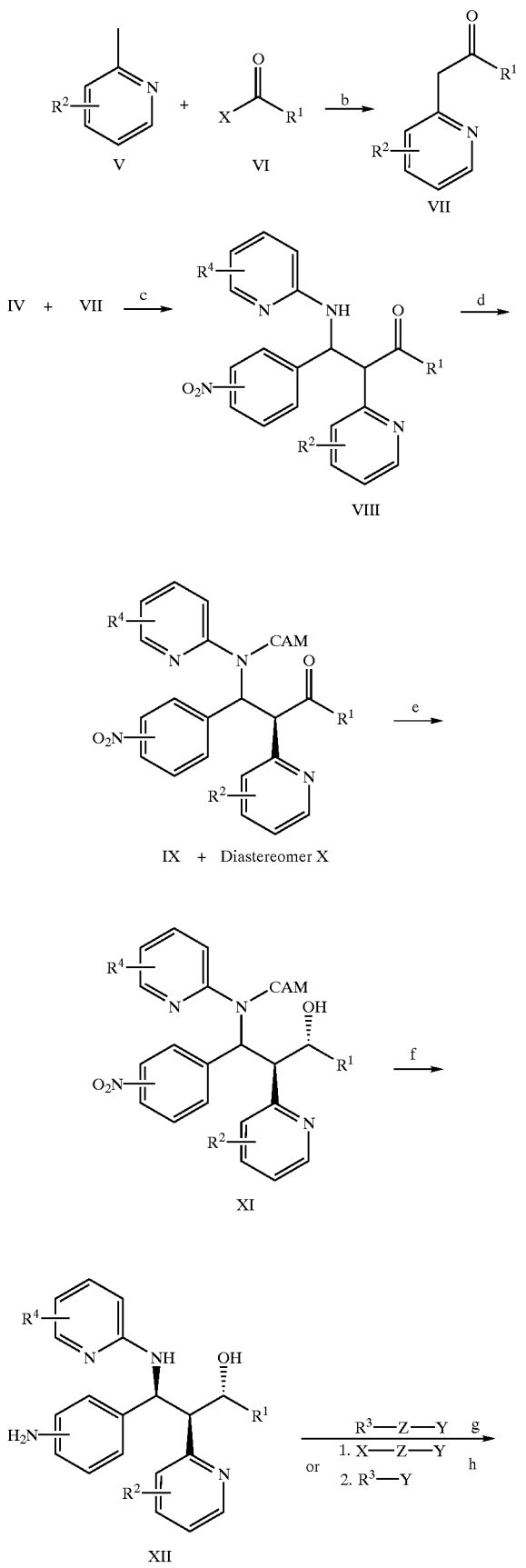

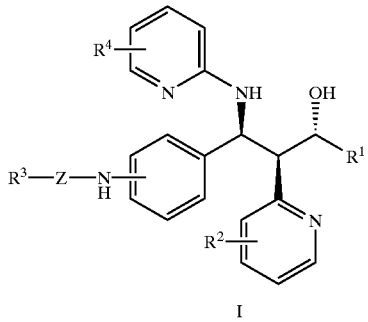

Shown above is a process for the preparation of compounds of formula I, wherein $R^4$-substituted imines are prepared from amines of type II and aldehydes of type III, $R^4$ having the meaning given for formula I. To this end, for example, the amine II and the aldehyde III are reacted in substance or in a suitable solvent such as ethanol, toluene or acetic acid without or with addition of an acid, for example p-toluenesulfonic acid, at temperatures of 20°–150° C. (a).

Keto compounds of formula VII which are substituted by radicals $R^1$ and $R^2$, where $R^1$ and $R^2$ have the meanings given in formula I, are prepared by processes known from the literature or similarly to such processes. For example, picolin derivatives V are metalated with a suitable base, such as n-butyllithium, and reacted in tetrahydrofuran or another suitable solvent with the corresponding carboxylic acid derivatives VI, for example as carboxylic dialkylamides or carboxylic esters (radical X), at temperatures between −80° and 20° C. (b).

Compounds of type VIII are obtained by reacting imines of type IV and ketones of type VII, in each case substituted with radicals $R^1$, $R^2$ and $R^4$, whereby $R^1$, $R^2$ and $R^4$ have the meaning given for formula I. This reaction can be carried out, for example, by mixing the two compounds in substance, without solvent, and subsequent heating, or in a suitable solvent such as methylene chloride, ethanol, toluene, diglyme or tetradecane at temperatures from 20° C. to 150° C. (c).

The racemic compounds of type VIII are resolved into the pure diastereomers of types IX and X with the aid of a chiral column (for example using camphanic acid, pentaacetylgluconic acid, camphor-10-sulphonic acid, O-methylmandelic acid or lactic acid), by crystallization, or by chromatography (d).

The keto compounds of type IX or X are reduced in a suitable solvent, such as, for example, methanol, THF or THF/water, using $NaBH_4$ or another suitable reducing agent, at temperatures between −30° and +40° C. to give hydroxy compounds of type XI, it being possible for these compounds to be substituted by the radicals $R^1$, $R^2$ and $R^4$, $R^1$, $R^2$ and $R^4$ having the meaning given for formula I (e).

The chiral column was cleaved in a suitable solvent such as, for example, methanol, ethanol, THF or THF/water, under basic or acidic conditions, such as, for example, using KOH, NaOH or HCl. The nitro group was subsequently reduced to the amine by processes known from the literature, and compounds of type XII with the radicals $R^1$, $R^2$ and $R^4$ are obtained (f).

The amino compounds of type XII are reacted with the alkyl or acyl radicals $R^3$—Z—Y, where Y represents a leaving group, using methods known from the literature, and compounds of the formula I are obtained (g). If X—Z—Y, where X is a protective group, is employed as the alkyl or acyl radical, intermediates are obtained which can be reacted with further alkyl or acyl radicals $R^3$—Y to give compounds of the formula I (h).

BRIEF DESCRIPTION OF THE DRAWING

FIG. 1 illustrates the stereochemistry of Example Ih as determined by X-ray crystallography.

The compounds of formula I and their pharmaceutically acceptable salts and physiologically functional derivatives are ideal pharmaceuticals for the treatment of disorders of the lipid metabolism, in particular of hyperlipidemia. The compounds of formula I are also suitable for influencing the serum cholesterol level and for the prevention and treatment of arteriosclerotic phenomena. If appropriate, the compounds may also be administered in combination with statins such as, for example, simvastatin, fluvastatin, pravastatin, cerivastatin, lovastatin or atorvastin. The following findings confirm the pharmacological efficacy of the compounds according to the invention.

The compounds according to the invention were tested in a biotest by determining the inhibition of [$^3$H]-taurocholate uptake in rabbit ileum cuticular layer membrane vesicles. The inhibitory test was carried out as follows:

1. Preparation of Rabbit Ileum Cuticular Layer Membrane Vesicles

Cuticular layer membrane vesicles were prepared from ileum cells by the so-called $Mg^{2+}$ precipitation method. Male New Zealand rabbits (body weight 2 to 2.5 kg) were sacrificed by intravenous injection of 0.5 ml T61®, an aqueous solution of 2.5 mg of tetracaine-HCl, 100 mg of embutramide and 25 mg of mebezonium iodide. The ileum was removed and washed with ice-cold physiological saline. The terminal 7/10th of the ileum (measured in the oral-rectal direction, i.e., the terminal ileum, which contains the active $Na^+$-dependent bile acid transport system) were used for preparing the cuticular layer membrane vesicles. The intestines were frozen in polymer bags at −80° C. under nitrogen. To prepare the membrane vesicles, the frozen intestines were defrosted in a water bath at 30° C. The mucosa was scraped off and suspended in 60 ml of ice-cold 12 mM TRIS/HCl buffer (pH 7.1)/300 mM mannitol, 5 mM EGTA/10 mg/l phenylmethylsulfonyl fluoride/1 mg/l soybean trypsin inhibitor (32 (U/mg)/0.5 mg/l bovine lung trypsin inhibitor (193 U/mg)/5 mg/l bacitracin. After the mixture had been diluted to 300 ml with ice-cold distilled water, it was homogenized in an Ultraturrax (rod 18, IKA Werk Staufen, Germany) for 3 minutes at 75% of maximum speed, with ice-cooling. After 3 ml of 1 M $MgCl_2$ solution had been added (final concentration 10 mM), the mixture was left to stand at 0° C. for exactly 1 minute. The addition of $Mg^{2+}$ causes the cell membranes to aggregate and precipitate with the exception of the cuticular layer membranes. After centrifugation for 15 minutes at 3000×g (5000 rpm, SS-34 rotor), the precipitate was discarded, and the supernatant, which contains the cuticular layer membranes, was centrifuged for 30 minutes at 48,000×g (20,000 rpm, SS-34 rotor). The supernatant was discarded, and the precipitate was rehomogenized in 60 ml of 12 mM TRIS/HCl buffer (pH 7.1)/60 mM mannitol, 5 mM EGTA using a Potter Elvejhem homogenizer (Braun, Melsungen, 900 rpm, 10 strokes). After addition of 0.1 ml of 1 M $MgCl_2$ solution and incubation for 15 minutes at 0° C., the mixture was again centrifuged for 15 minutes at 3000×g. The supernatant was subsequently centrifuged for a further 30 minutes at 48,000×g (20,000 rpm, SS-34 rotor). The precipitate was taken up in 30 ml of 10 mM TRIS/HEPES buffer (pH 7.4)/300 mM mannitol and resuspended to homogeneity by 20 strokes in a Potter Elvejhem homogenizer at 1000 rpm.

After centrifugation for 30 minutes at 48,000×g (20,000 rpm, SS-34 rotor), the precipitate was taken up in 0.5 to 2 ml of TRIS/HEPES buffer (pH 7.4)/280 mM mannitol (final concentration 20 mg/ml) and resuspended with the aid of a Tuberkulin syringe using a 27-gauge cannula. The vesicles were either used immediately after the preparation for transport tests or stored in 4-mg portions in liquid nitrogen at −196° C.

2. Inhibition of $Na^+$-dependent [$^3$H]taurocholate Uptake in Ileum Cuticular Layer Membrane Vesicles The uptake of substrates into the above-described cuticular layer membrane vesicles was determined by means of the so-called membrane filtration technique. 10 μl of the vesicular suspension (100 μg protein) were pipetted as drops onto the wall of a polystyrol incubation tube (11×70 mm), which contained the incubation medium together with the relevant ligands (90 μl). The incubation medium contained 0.75 μl=0.75 Ci [$^3$H(G)]taurocholate (specific activity: 2.1 Ci/mMol),/0.5 μl 10 mM taurocholate/8.75 μl sodium transport buffer (10 mM TRIS/HEPES, (pH 7.4)/100 mM mannitol/100 mM NaCl) (Na-T-P) or 8.75 μl potassium transport buffer (10 mM TRIS/HEPES (pH 7.4)/100 mM mannitol/100 mM KCl) (K-T-P) and 80 μl of the inhibitor solution in question, dissolved in Na/T buffer or K/T buffer, respectively, depending on the experiment. The incubation medium was filtered through a polyvinylidene fluoride membrane filter (SYHV LO 4NS, 0.45 μm, 4 mm Ø, Millipore, Eschborn, Germany). The transport measurement was started by mixing the vesicles with the incubation medium. The taurocholate concentration in the incubation batch was 50 μM. After the desired incubation time (normally 1 minute), the transport was stopped by adding 1 ml of ice-cold quenching solution (10 mM TRIS/HEPES, (pH 7.4)/150 mM KCl). The resulting mixture was removed immediately by suction in a vacuum of 25 to 35 mbar through a cellulose nitrate membrane filter (ME 25, 0.45 μm, diameter 25 mm, Schleicher & Schuell, Dassell, Germany). The filter was rinsed with 5 ml of ice-cold quenching solution.

To measure the uptake of radiolabeled taurocholate, the membrane filter was dissolved in 4 ml of the scintillator Quickszint 361 (Zinsser Analytik GmbH, Frankfurt, Germany), and the radioactivity was measured by liquid scintillation measurement in a TriCarb 2500 (Canberra Packard GmbH, Frankfurt, Germany) apparatus. After the apparatus had been calibrated with the aid of standard samples and any chemiluminescence which may have been present had been corrected, the measured values were obtained as dpm (decompositions per minute).

The control values were determined in each case in Na-T-P and K-T-P. The difference between the uptake in Na-T-P and K-T-P represented the $Na^+$-dependent transport. The term $IC_{50}$ $Na^+$ was used to designate the inhibitor concentration at which the $Na^+$-dependent transport was inhibited by 50% relative to the control.

The pharmacological data encompass a test series in which the interaction of the compounds according to the invention with the intestinal bile acid transport system in the terminal ileum was investigated. The results are shown in Table 1.

Tables 1 and 2 show measured values (Biolog. Test) of the inhibition of [$^3$H]-taurocholate uptake in rabbit ileum cuticular layer membrane vesicles. The data given are the quotients of the $IC_{50Na}$ values of the reference substance as taurochenodesoxycholate (TCDC) and the test substance in question.

TABLE 1

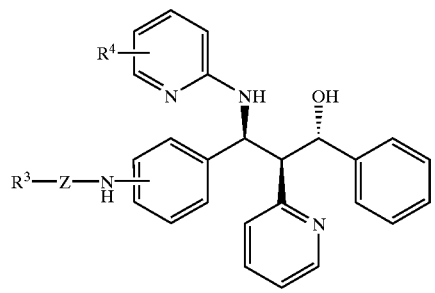

| Ex. | R³ | Z | R⁴ | R³—Z—NH— | Empirical formula (molecular weight) | MS | Bio. Test |
|---|---|---|---|---|---|---|---|
| 1 | Gluconic acid | — | H | ortho | $C_{31}H_{34}N_4O_7$ (574.63) | 575.3 M + H⁺ | 1.09 |
| 2 | Gluconic acid | —NH—CH₂—CH₂—CH₂— | H | ortho | $C_{34}H_{41}N_5O_7$ (631.73) | 632.4 M + H⁺ | 0.24 |
| 3 | Gluconic acid | -(L)-Pro- | H | ortho | $C_{36}H_{41}N_5O_8$ (671.75) | 672.4 M + H⁺ | 0.15 |
| 4 | Gluconic acid | -(L)-Phe-(L)-Pro- | H | ortho | $C_{45}H_{50}N_6O_9$ (818.92) | 819.5 M + H⁺ | 1.69 |
| 5 | Gluconic acid | —NH—CH₂-(trans-1,4-cyclohexyl)-CO— | H | ortho | $C_{39}H_{47}N_5O_8$ (713.83) | 714.4 M + H⁺ | 1.56 |
| 6 | Gluconic acid | —NH-(trans-1,4-cyclohexyl)-CO— | H | ortho | $C_{38}H_{45}N_5O_8$ (699.80) | 700.4 M + H⁺ | 1.19 |
| 7 | Penta-O-acetylgluconic acid | — | H | ortho | $C_{41}H_{44}N_4O_{12}$ (784.81) | 785.4 M + H⁺ | 0.44 |
| 8 | Penta-O-acetylgluconic acid | —NH—(CH₂)₁₀—CO— | H | ortho | $C_{52}H_{65}N_5O_{13}$ (968.11) | 968.6 M + H⁺ | 0.83 |
| 9 | Gluconic acid | —NH—(CH₂)₁₀—CO— | H | ortho | $C_{42}H_{55}N_5O_8$ (757.92) | 758.5 M + H⁺ | 1.78 |
| 10 | Gluconic acid | —NH—(CH₂)₁₁—CO— | H | ortho | $C_{43}H_{57}N_5O_8$ (771.95) | 772.5 M + H⁺ | 1.53 |
| 11 | Gluconic acid | —NH—(CH₂)₇—CO— | H | ortho | $C_{39}H_{49}N_5O_8$ (715.84) | 716.4 M + H⁺ | 1.59 |
| 12 | Gluconic acid | —NH—(CH₂)₆—CO— | H | ortho | $C_{38}H_{47}N_5O_8$ (701.82) | 702.4 M + H⁺ | 0.29 |
| 13 | Gluconic acid | —NH—(CH₂)₅—CO— | H | ortho | $C_{37}H_{45}N_5O_8$ (687.79) | 688.4 M + H⁺ | 0.28 |
| 14 | Gluconic acid | —NH—(CH₂)₄—CO— | H | ortho | $C_{36}H_{43}N_5O_8$ (673.76) | 674.4 M + H⁺ | 0.23 |
| 15 | Glucamine | —CO—(CH₂)₂—CO— | H | ortho | $C_{35}H_{41}N_5O_8$ (659.74) | 660.4 M + H⁺ | 0.19 |
| 16 | Glucamine | —CO—(CH₂)₈—CO— | H | ortho | $C_{41}H_{53}N_5O_8$ (743.90) | 744.5 M + H⁺ | 0.86 |
| 17 | Glucamine | —CO—(CH₂)₉—CO— | H | ortho | $C_{42}H_{55}N_5O_8$ (757.92) | 758.5 M + H⁺ | |
| 18 | Glucamine | —CO—(CH₂)₁₀—CO— | H | ortho | $C_{43}H_{57}N_5O_8$ (771.95) | 772.5 M + H⁺ | 1.21 |
| 19 | Glucamine | —CO—(CH₂)₁₂—CO— | H | ortho | $C_{45}H_{61}N_5O_8$ (800.00) | 800.6 M + H⁺ | 2.73 |
| 20 | Glucamine | —CO—(CH₂)₁₄—CO— | H | ortho | $C_{47}H_{65}N_5O_8$ (828.06) | 828.7 M + H⁺ | 0.32 |
| 21 | Glucosamine | —CO—(CH₂)₂—CO— | H | ortho | $C_{35}H_{39}N_5O_8$ (657.72) | 658.4 M + H⁺ | 0.26 |
| 22 | Glucamine | —(CH₂)₁₁—CO— | H | ortho | $C_{43}H_{59}N_5O_7$ (757.97) | 758.5 M + H⁺ | |
| 23 | Glucamine | —(CH₂)₁₀—CO— | H | ortho | $C_{42}H_{57}N_5O_7$ (743.94) | 744.5 M + H⁺ | |
| 24 | Glycerolamine | —(CH₂)₁₀—CO— | H | ortho | $C_{39}H_{51}N_5O_4$ (653.86) | 654.4 M + H⁺ | |
| 25 | HO—SO₂— | — | H | ortho | $C_{25}H_{24}N_4O_4S$ (476.55) | 477.3 M + H⁺ | |
| 26 | HO—SO₂— | —NH—(CH₂)₁₁—CO— | H | ortho | $C_{37}H_{47}N_5O_5S$ (673.87) | 674.4 M + H⁺ | 1.72 |
| 27 | HO—SO₂— | —NH—(CH₂)₁₀—CO— | H | ortho | $C_{36}H_{45}N_5O_5S$ (659.85) | 660.4 M + H⁺ | |
| 28 | HO—SO₂— | -(L)-Phe-(L)-Pro- | H | ortho | $C_{39}H_{40}N_6O_6S$ (720.85) | 721.5 M + H⁺ | 1.56 |
| 29 | Glucuronic acid | —O—CH₂—CO— | H | ortho | $C_{33}H_{34}N_4O_9$ (630.65) | 631.3 M + H⁺ | |

TABLE 1-continued

| Ex. | R³ | Z | R⁴ | R³—Z—NH— | Empirical formula (molecular weight) | MS | Bio. Test |
|---|---|---|---|---|---|---|---|
| 30 | Glucuronic acid | —O—CH₂(CH₃)₂—CO— | H | ortho | $C_{35}H_{38}N_4O_9$ (658.70) | 659.3 M + H⁺ | 0.42 |
| 31 | Glucuronic acid | —O—(CH₂)₁₁—CO— | H | ortho | $C_{43}H_{54}N_4O_9$ (770.92) | 771.5 M + H⁺ | |

TABLE 2

| Ex. | R¹ | R³ | Z | Isomer | Empirical formula (molecular weight) | MS | Bio. Test |
|---|---|---|---|---|---|---|---|
| 43 | 3,5-dimethyl-isoxazolyl-4-yl | gluconic acid | NH—(CH₂)₁₀—CO | I | $C_{41}H_{56}N_6O_9$ (776.9) | 777.4 M + H⁺ | 0.45 |
| 44 | 3,5-dimethyl-isoxazolyl-4-yl | gluconic acid | NH—(CH₂)₁₀—CO | IA¹ | $C_{41}H_{56}N_6O_9$ (776.9) | 777.4 M + H⁺ | 0.49 |
| 45 | 3,5-dimethyl-isoxazolyl-4-yl | gluconic acid | NH—(CH₂)₁₀—CO | IB¹ | $C_{41}H_{56}N_6O_9$ (776.9) | 777.4 M + H⁺ | |
| 46 | 3,5-dimethyl-isoxazolyl-4-yl | gluconic acid | NH—(CH₂)₁₀—CO | II | $C_{41}H_{56}N_6O_9$ (776.9) | 777.4 M + H⁺ | |
| 47 | 3,5-dimethyl-isoxazolyl-4-yl | gluconic acid | NH—(CH₂)₁₀—CO | III | $C_{41}H_{56}N_6O_9$ (776.9) | 777.4 M + H⁺ | |
| 48 | 3,5-dimethyl-isoxazolyl-4-yl | gluconic acid | NH—(CH₂)₁₀—CO | IV | $C_{41}H_{56}N_6O_9$ (776.9) | 777.4 M + H⁺ | |
| 49 | 2,4-dimethyl-thiazol-5-yl | gluconic acid | NH—(CH₂)₁₀—CO | I | $C_{41}H_{56}N_6O_8S$ (793.0) | 793.4 M + H⁺ | 0.24 |
| 50 | 2,4-dimethyl-thiazol-5-yl | gluconic acid | NH—(CH₂)₁₀—CO | II | $C_{41}H_{56}N_6O_8S$ (793.0) | 793.4 M + H⁺ | |
| 51 | 2,4-dimethyl-thiazol-5-yl | gluconic acid | NH—(CH₂)₁₀—CO | III | $C_{41}H_{56}N_6O_8S$ (793.0) | 793.4 M + H⁺ | |
| 52 | 2,5-dimethyl-oxazol-4-yl | gluconic acid | NH—(CH₂)₁₀—CO | I | $C_{41}H_{56}N_6O_9$ (776.9) | 777.4 M + H⁺ | 0.31 |
| 53 | 5-pentyl-isoxazol-3-yl | gluconic acid | NH—(CH₂)₁₀—CO | I² | $C_{44}H_{62}N_6O_9$ (819.0) | 819.6 M + H⁺ | |
| 54 | 5-pentyl-isoxazol-3-yl | gluconic acid | NH—(CH₂)₁₀—CO | II² | $C_{44}H_{62}N_6O_9$ (819.0) | 819.6 M + H⁺ | |
| 55 | 3,5-dimethyl-isoxazolyl-4-yl | penta-O-acetyl gluconic acid | — | I | $C_{40}H_{45}N_5O_{13}$ (803.8) | 804.1 M + H⁺ | 0.24 |
| 56 | 3,5-dimethyl-isoxazolyl-4-yl | penta-O-acetyl gluconic acid | — | II | $C_{40}H_{45}N_5O_{13}$ (803.8) | 804.1 M + H⁺ | |
| 57 | 3,5-dimethyl-isoxazolyl-4-yl | gluconic acid | — | II | $C_{30}H_{35}N_5O_8$ (593.6) | 594.4 M + H⁺ | |
| 58 | 3,5-dimethyl-isoxazolyl-4-yl | gluconic acid | — | I | $C_{30}H_{35}N_5O_8$ (593.6) | 594.4 M + H⁺ | |
| 59 | 5-methyl-isoxazol-3-yl | gluconic acid | NH—(CH₂)₁₀—CO | —³ | $C_{40}H_{54}N_6O_9$ (762.9) | 763.4 M + H⁺ | |
| 60 | 2,5-dimethyl-oxazol-4-yl | gluconic acid | — | —³ | $C_{31}H_{36}N_4O_8$ (592.6) | 594.2 M + H⁺ | |
| 61 | 5-methyl-isoxazol-3-yl | gluconic acid | — | I | $C_{29}H_{33}N_5O_8$ (579.6) | 580.2 M + H⁺ | |
| 62 | 2,4-dimethyl-thiazol-5-yl | penta-O-acetyl gluconic acid | — | I | $C_{40}H_{45}N_5O_{12}S$ (819.9) | 820.1 M + H⁺ | |
| 63 | 2,4-dimethyl-thiazol-5-yl | penta-O-acetyl gluconic acid | — | II | $C_{40}H_{45}N_5O_{12}S$ (819.9) | 820.1 M + H⁺ | |
| 64 | 2,4-dimethyl-thiazol-5-yl | gluconic acid | — | I | $C_{30}H_{35}N_5O_7S$ (609.7) | 610.2 M + H⁺ | |
| 65 | 2,4-dimethyl-thiazol-5-yl | gluconic acid | — | II | $C_{30}H_{35}N_5O_7S$ (609.7) | 610.2 M + H⁺ | |
| 66 | 3-(3-chlorophenyl)-5-methyl-isoxazol-4-yl | gluconic acid | — | —³ | $C_{35}H_{36}ClN_5O_8$ (690.2) | 690.2 M + H⁺ | |
| 67 | 3-(3-chlorophenyl)-5-methyl-isoxazol-4-yl | gluconic acid | NH—(CH₂)₁₀—O | —³ | $C_{46}H_{57}ClN_6O_9$ (873.4) | 873.3 M + H⁺ | |
| 68 | 4-methyl-2-(pyrid-4-yl)-thiazol-5-yl | penta-O-acetyl gluconic acid | — | —³ | $C_{44}H_{46}N_6O_{12}S$ (882.9) | 883.2 M + H⁺ | |

¹Enantiomers
²Diastereomer pair I or II
³Diastereomer mixture

Test for Gallstone Formation

1. Test Substance, Dose and Application

Example 9 of Table 1 (=A1) 100 mg/kg/d 0.1% in the feed

2. Aim

In this test, the cholesterol gallstone formation in gallstone-sensitive mice was investigated.

3. Materials and Methods

3.1 Animals and Housing

The experimental animals used are male C57L mice (Jackson Laboratories) with an average body weight of 25–30 g at the beginning of the adaptation. The animals were randomly divided into 4 groups (n=10, groups 2 and 3 n=15). Starting at the beginning of the treatment, the mice were either fed a standard rodent feed by Altromin (group 1), or a lithogenic diet by Altromin (groups 2–4); this diet was composed as follows: 15% butter, 1% cholesterol, 50% sugar, 20% casein, 0.5% cholic acid, 5% mineral mix, 2.5% vitamin mix, 2% corn oil, corn starch to 100%.

The animals were weighed weekly, and the food consumption was determined by continuous weighings before and after, whereby the dose was calculated.

3.2. Final Examination

After 11 and 13 weeks, respectively, the animals of each group were sacrificed and the gallbladders subsequently prepared. Gallstones in the gallbladder were then recorded. The gallbladder was dissected, the weight was determined, and the composition of the bile and the gallstones was analyzed. The results are given in Table 3.

TABLE 3

Gallstone formation results

| Group | Feed | Dose (mg/kg/d) | Treatment time (weeks) | Frequency of gallstones (n/n) |
|---|---|---|---|---|
| 1 | Normal feed | — | 13 | 0/10 |
| 2 | Lithogenic diet | — | 11 | 5/15 |
| 3 | Lithogenic diet | — | 13 | 5/15 |
| 4 | Lithogenic diet + Example 9 | 100 | 13 | 0/10 |

4. Results

The measurement values in Table 3 reveal that the compounds according to the invention efficiently prevent the formation of gallstones. They are therefore suitable both for the prophylaxis and for the treatment of gallstones.

Selected examples of Table 1, full structure

Ex. 2

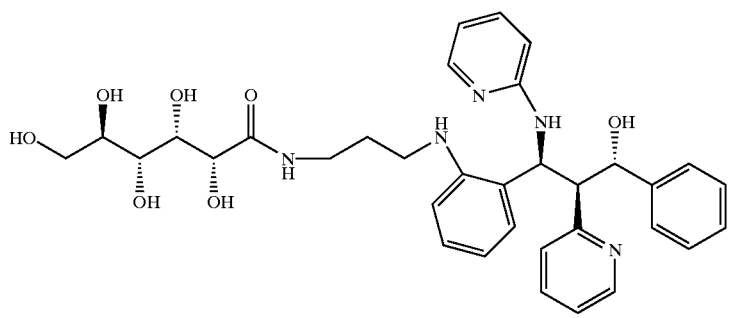

Ex. 15

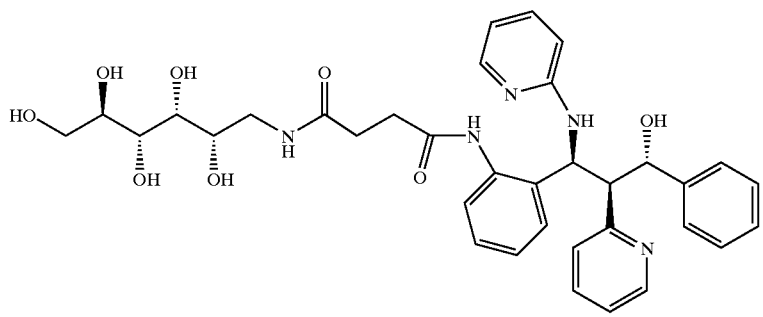

Ex. 24

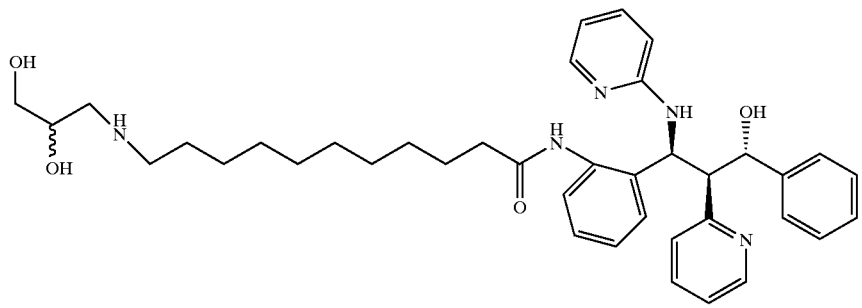

-continued

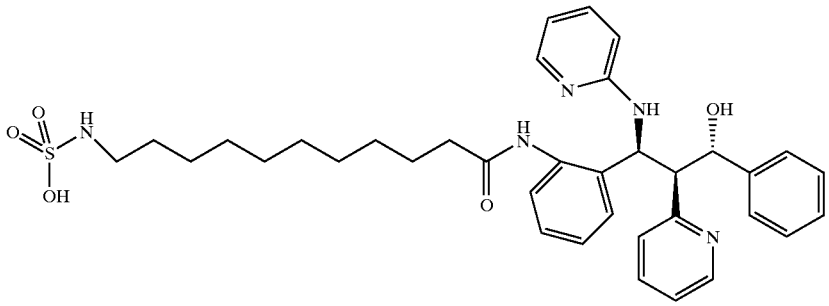
Ex. 27

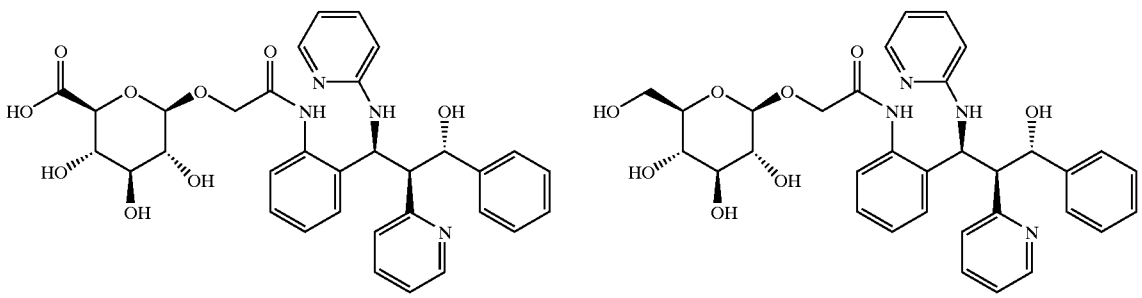
Ex. 29    Ex. 33

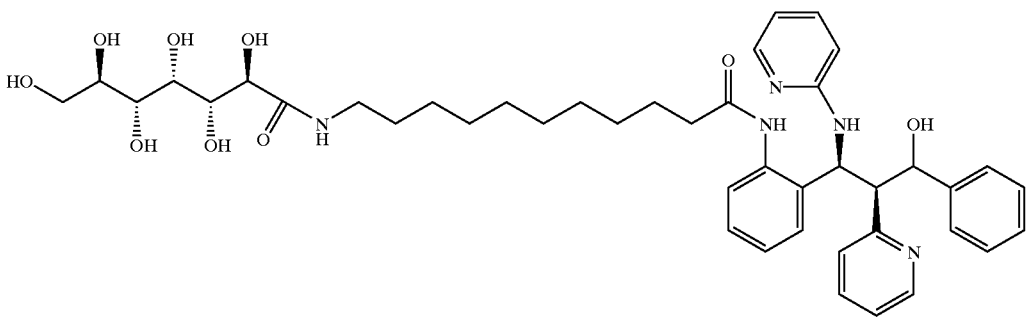
Ex. 41

The examples which follow are intended to illustrate the invention in greater detail, without limiting the latter to the products and embodiments described in the examples.

EXAMPLE A1 (=Ex. 9 of Table 1)

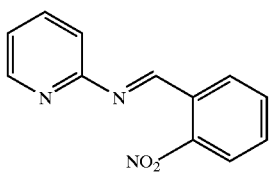
1a 0.7 g of p-toluenesulfonic acid were added to a solution of 25 g (266 mmol of 2-aminopyridine and 40 g (265 mmol) of 2-nitrobenzaldehyde in 300 ml of toluene, and the mixture was refluxed for 6 hours. After cooling, half of the solvent was removed in vacuo and left to stand overnight. The resulting precipitate was filtered off with suction, washed with cold toluene and dried in vacuo. Subsequent recrystallization from n-heptane/ethyl acetate 2:1 gave 48.8 g (81%) of the imine.

$C_{12}H_9N_3O_2$ (227.2) MS (FAB) 228.2 M+H$^+$

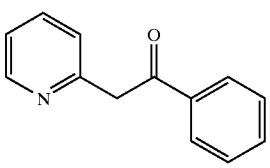
1b 250 ml of n-butyllithium (15% in hexane) were added dropwise at −55° C. to a solution of 50 g (0.54 mol) of 2-picolin in 770 ml of tetrahydrofuran, and the mixture was stirred for 10 minutes. The mixture was subsequently warmed to 0° C. and, after a further 30 minutes, cooled to −55° C. A solution of 77 g (0.52 mol) of N,N-dimethylbenzamide in 570 ml of tetrahydrofuran was subsequently slowly added dropwise. After the addition, the mixture was warmed to room temperature and stirred for 1 hour. After addition of 500 ml of water and 35 ml of concentrated HCl, the organic phase was separated off and the aqueous phase was extracted twice with ethyl acetate. After drying over MgSO$_4$, it was concentrated in vacuo and the residue was distilled in a high vacuum. Boiling point 134–136° C./0.3 mbar. Yield: 47.5 g (47%) of the ketone.

$C_{13}H_{11}NO$ (197.2) MS (FAB) 198.1 M+H$^+$

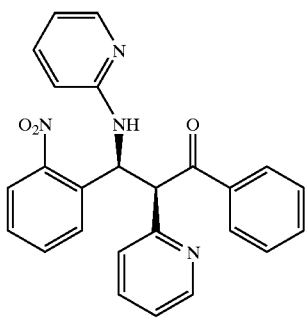

1c

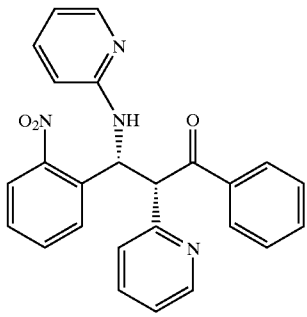

1d 200 g (0.89 mol) of the imine of Example 1a and 171 g (0.88 mol) of the ketone of Example 1b were dissolved in dichloromethane under reflux. After the starting materials have dissolved, the mixture was allowed to cool to room temperature. The reaction solution was diluted with 600 ml of ethyl acetate and 300 ml of n-heptane. This solution was filtered with the aid of a glass frit (1 liter) filled with 500 ml of flash silica gel, and washed with 500 ml of n-heptane/ethyl acetate (1:2). The filtrate was concentrated, and 370 g of crude product were obtained. The crude product was a mixture of all four possible stereoisomers. The two desired cis products 1c/d were obtained by crystallization from ethanol. To this end, the crude product was dissolved in 600 ml of ethanol and left to stand for two days at room temperature; this gave 190 g of product 1c/d. A further 106 g of product 1c/d was isolated from the mother liquor after a further five days. The stereoisomers exist in solution in an equilibrium. The pair of enantiomers 1c/1d was sparingly soluble in ethanol and crystallized out of solution, while the trans pair of enantiomers was soluble in ethanol. Yield 296 g (79%) 1c/1d as yellowish crystals.

$C_{25}H_{20}N_4O_3$ (424.2) MS (FAB) 425.1 M+H$^+$

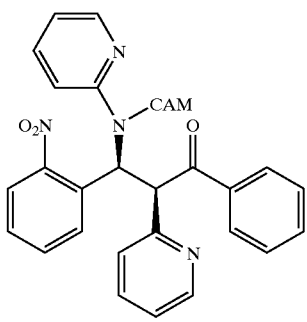

1e

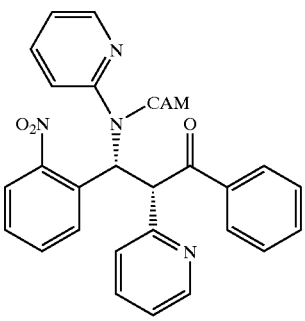

1f 33 g (153 mmol) of (−)-camphanic chloride CAMCl (Fluka) were dissolved in 500 ml of methylene chloride and the solution was cooled to 10° C. 50 ml of triethylamine were added to this solution. Then, 52.3 g (123 mmol) of crystalline ketone of Example 1c/d were slowly added in such a way that the reaction temperature does not exceed 20° C. The end of the reaction was monitored by thin layer chromatography (approx. 30 minutes). The reaction solution was diluted with 500 ml of ethyl acetate and washed with water, dried over MgSO$_4$, filtered and concentrated. The organic phase was concentrated until 1f started to crystallize. It was then filtered, and 32.5 g (44%) of 1f were obtained as a white solid. The mother liquor was diluted with 500 ml of n-heptane/ethyl acetate (4:1) and reconcentrated until product 1e started to crystallize again. This gave 32 g (44%) of 1e as colorless crystals.

$C_{35}H_{32}N_4O_6$ (604.7) MS (FAB) 605.3 M+H$^+$

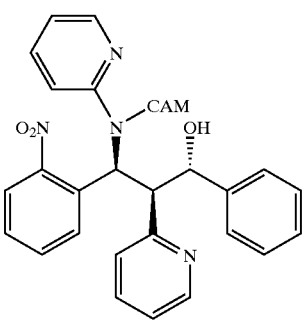

1g

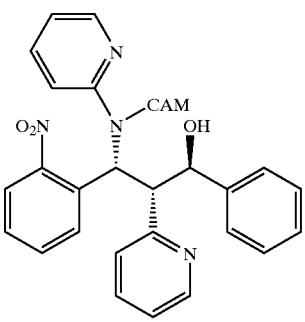

1h 8.5 g (14.1 mmol) of the keto compound of Example 1e were dissolved in 150 ml of THF/water 10:1, the solution was treated with 2.0 g (53 mmol) of sodium borohydride and everything was stirred for 10 hours at room temperature. The pH was brought to 1 using 2 N HCl and the mixture was stirred for 30 minutes at 50° C. After cooling, the reaction mixture was rendered alkaline with 2 N NaOH and extracted twice with ethyl acetate. The organic phases were dried over MgSO₄ and concentrated until the crystallization of 1 g started. Yield: 3.6 g of white crystals. The mother liquor was concentrated further, and a second fraction of 1 g (2.45 g) was isolated. The total yield was 6.05 g (71%) of 1 g. 1f was reacted in an analogous procedure, which gave 1h as colorless crystals. The stereochemistry of Example 1h was determined by X-ray structural analysis as shown in FIG. 1.
C₃₅H₃₄N₄O₆ (606.7) MS (FAB) 607.3 M+H⁺ n-heptane, which gave 25.2 g of 1i as colorless crystals (68% in 2 steps). Also, the mother liquor gave 10 g of an amorphous fraction of 1i, with a purity of 80–90%.

C₂₅H₂₄N₄O (396.49) MS (FAB) 397.2 M+H⁺

Optical rotation $(\alpha)_D^{20}=+59°$ (C=1, in CH₂Cl₂)

1j

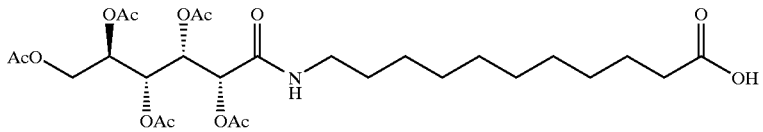

1i

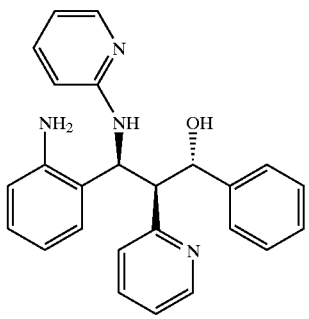

8.0 g (18.8 mmol) of penta-O-acetyl-D-gluconic chloride (*Org. Synth.*, Volume 5, 887) were added to a suspension of 8.0 g (40 mmol) of 11-aminoundecanoic acid (Fluka) in 150 ml of anhydrous DMF. This suspension was stirred vigorously for 20 hours at room temperature. 500 ml of ethyl acetate and 200 ml of water were then added. The aqueous phase was reextracted with 250 ml of ethyl acetate. The combined organic phase was washed three times with sodium chloride solution, dried over MgSO₄, filtered and concentrated, yielding 9.5 g (86%) of 1j as colorless oil. Thin layer chromatography in a mobile phase of methylene chloride/methanol/concentrated ammonia, 30/10/3, gave an R_f of 0.8.

C₂₇H₄₃NO₁₃ (589.6) MS (FAB) 590.4 M+H⁺

1k

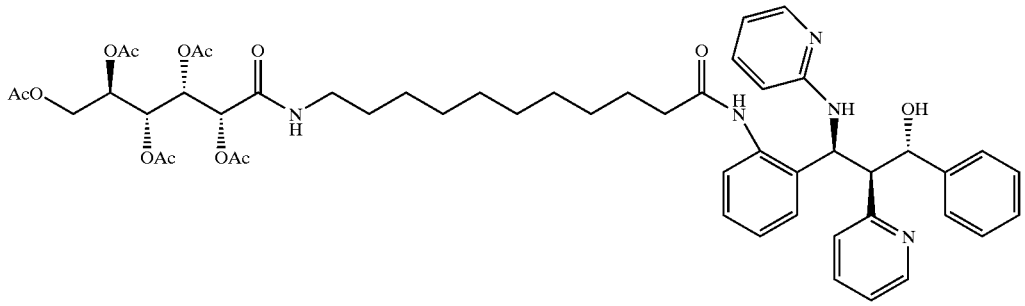

50 g of KOH were dissolved in 500 ml of ethanol. 57 g (94 mmol) of the camphanic acid derivative 1 g, dissolved in 500 ml of methylene chloride, were added to this solution at room temperature. After 2 hours, the mixture was subjected to aqueous work-up, which gives 44.3 g of crude product. This crude product was dissolved in 750 ml of methylene chloride, and 7.5 g of palladium on charcoal (10%) were added. After a hydrogenation time of 10 hours, the hydrogen uptake was complete (approximately 6.5 l). The reaction solution was filtered through silica gel and washed with 400 ml of methanol. After the solvent was evaporated on a rotary evaporator, 40 g of crude product were obtained. This was recrystallized from ethyl acetate/

27 g (45.8 mmol) of 1j and 16 g (40.3 mmol) of 1i were dissolved in 300 ml of DMF (dimethylformamide). 20 g (61 mmol) of TOTU (Fluka), 7 g (50 mmol) of oxime (ethyl hydroxyiminocyanoacetate; Fluka) and 17 ml (150 mmol) of NEM (4-ethylmorpholine) were added in succession. After one hour at room temperature, the mixture was diluted with 1000 ml of ethyl acetate and washed three times with water. The organic phase was dried over MgSO₄, filtered and concentrated. The residue was purified by means of flash chromatography (ethyl acetate/n-heptane 1:1), and 37.1 g (95%) of 1k were obtained as an amorphous solid.

C₅₂H₆₅N₅O₁₃ (968.1) MS (FAB) 968.7 M+H⁺

A1 (= Ex. 9 of Table 1)

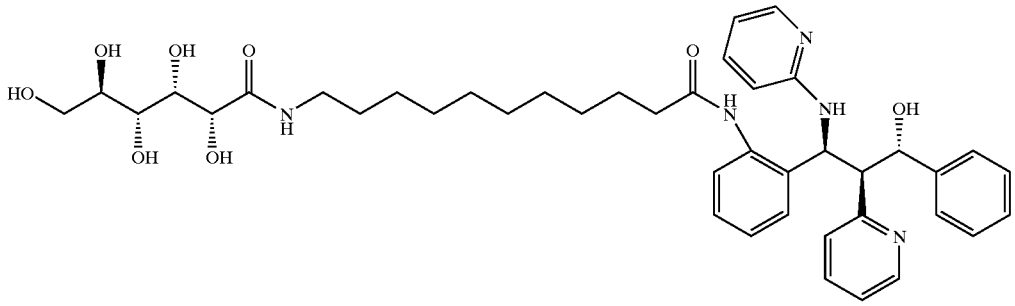

37.1 g (38.3 mmol) of 1k were dissolved in 300 ml of methanol. After addition of 3 ml of a methanolic 1 M sodium methoxide solution, the mixture was left to stand for one hour at room temperature. It was then neutralized with methanolic HCl solution and concentrated. The residue was purified by flash chromatography (methylene chloride/methanol/concentrated ammonia 30/5/1), and 24.5 g (84%) of A1 (=Ex. 9 of Table 1) were obtained as amorphous solid.

$C_{42}H_{55}N_5O_8$ (757.9) MS (FAB) 758.4 M+H$^+$ 10.0 g (25.0 mmol) of 1i and 13.5 g (50.0 mmol) of 11-bromoundecanoic acid (Fluka) were dissolved in 100 ml of DMF (dimethylformamide). 15 g (45.7 mmol) of TOTU (Fluka) and 17 ml (150 mmol) of NEM (4-ethyl-morpholine) were added in succession at 0° C. After one hour at 0° C., the mixture was diluted with 500 ml of ethyl acetate and washed three times with water. The organic phase was dried over MgSO$_4$, filtered and concentrated. The residue was purified by means of flash chromatography (ethylacetate/n-heptane 2:1), and 9.9 g (62%) of 2a were obtained as amorphous solid.

$C_{36}H_{43}BrN_4O_2$ (643.7) MS (FAB) 643.3 M+H$^+$

A2 (= Ex. 23 of Table 1)

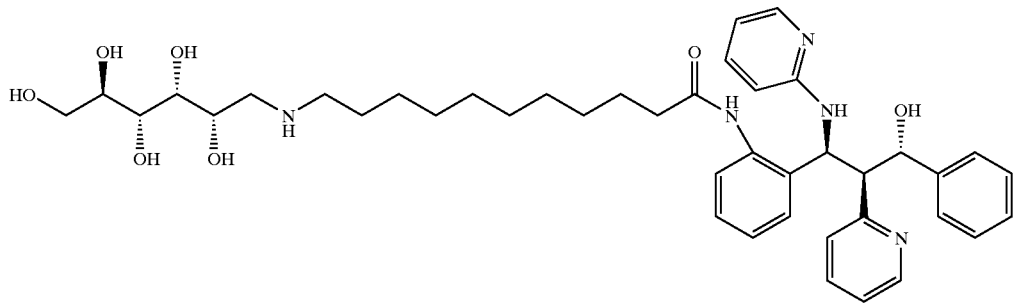

EXAMPLE A2 (=Ex. 23 of Table 1)

2a

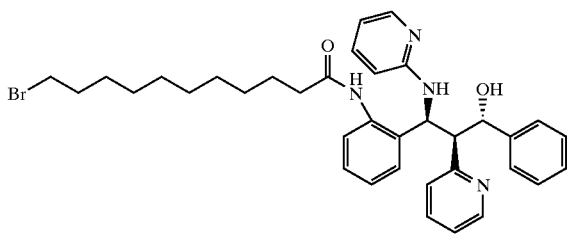

9.87 g (15.3 mmol) of 2a were dissolved in 200 ml of DMF. After addition of 14 g (77 mmol) of glucamine (Fluka), the solution was heated for two hours at 80° C. It was then diluted with 500 ml of ethyl acetate and washed three times with water. The organic phase was dried over MgSO$_4$, filtered and concentrated. The residue was purified by means of flash chromatography (methylene chloride/methanol/concentrated ammonia 30/5/1), and 7.3 g (65%) of A2 were obtained as an amorphous solid.

$C_{42}H_{57}N_5O_7$ (743.9) MS (FAB) 744.4 M+H$^+$

EXAMPLE A3

3a

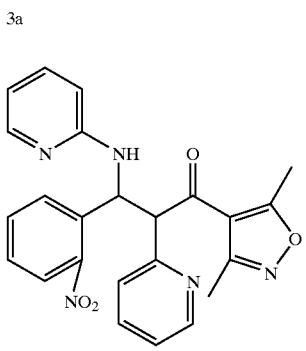

92 g (0.43 mol) of 1-(3,5-dimethylisoxazol-4-yl)-2-pyridin-2-yl-ethanone (prepared as described for Example 1b, but using ethyl 3,5-dimethylisoxazolylcarboxylate instead of N,N-dimethylbenzamide) were dissolved in 1200 ml of hot ethanol. 96.7 g of the imine of Example 1a were added at room temperature, and the reaction mixture was stirred for three days at room temperature. After a few hours, a pale yellow solid started to precipitate. In order to isolate the reaction product, the precipitated solid was filtered off, which provided 118.9 g (63%) of pale yellow crystals of melting point 139–140° C.

$C_{24}H_{21}N_5O_4$ (443.5) MS (FAB) 444.4 (M+H$^+$)

3b (strongly unpolar diastereomer)

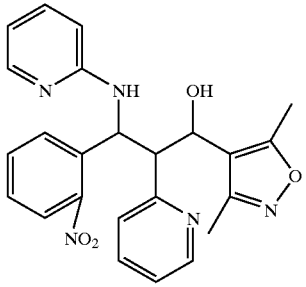

117 g (0.264 mol) of the ketone of Example 3a were reduced by means of sodium borohydride following the procedure described in Example 1g/h. The resulting crude product was purified by means of silica gel chromatography using a mixture of ethyl acetate/n-heptane in the ratio of 2:1 as the mobile phase. This gave 76 g (65%) of the strongly unpolar diastereomer of melting point 95° C.; in addition, small amounts of the other three possible diastereomers were also isolated.

$C_{24}H_{23}N_5O_4$ (445.5) MS (FAB) 446.3 (M+H$^+$)

3c (strongly unpolar diastereomer)

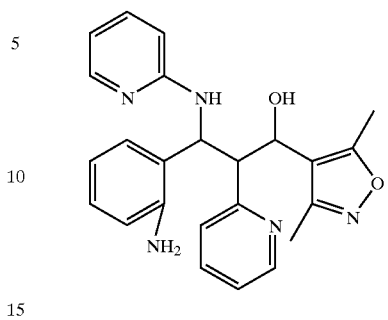

44.5 g (0.1 mol) of the aminopropanol of Example 3b were dissolved in 1500 ml of ethanol and treated at 20° C. with 570 ml of 15% strength aqueous TiCl$_3$ solution. After the addition has ended, the mixture was stirred for 2.5 hours at room temperature. For work-up, the reaction mixture was concentrated under reduced pressure, the residue which remains was extracted with dichloromethane/water and neutralized by adding NaHCO$_3$, and insoluble titanium hydroxide was filtered off. After the organic phase was dried and concentrated under reduced pressure, the remaining residue was filtered through a short silica gel column (mobile phase ethyl acetate). The remaining residue, after the eluant was removed, crystallized upon stirring with diethyl ether in the form of colorless crystals. This gave 33.2 g (80%) of colorless crystals with a melting point 115° C.

$C_{24}H_{25}N_5O_2$ (415.5) MS (FAB) 416.4 (M+H$^+$)

3d (= Ex. 55 of Table 2)

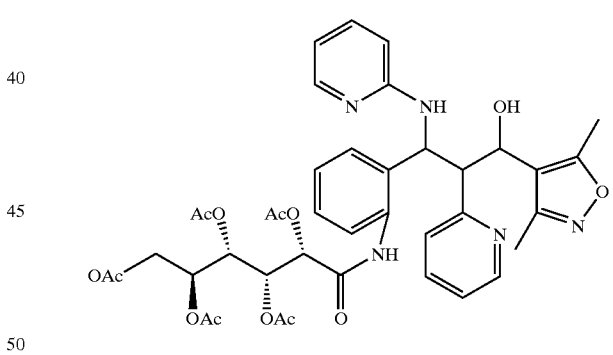

6.2 g (0.015 mol) of the amino compound of Example 3c (strongly unpolar diastereomer, which, in turn, was present as a pair of enantiomers) were dissolved in 100 ml of absolute DMF and treated with 6.1 g (0.015 mol) of pentaacetyl-D-gluconic acid (*Org. Synth.,* Volume 5, 887), 5.9 g of TOTU (Fluka), 2.1 g of ethyl hydroxyiminocyanoacetate and 5.9 ml of N-ethylmorpholine, with stirring. The reaction mixture was stirred for 20 hours at room temperature. For work-up, the solvent was removed under reduced pressure, and the resulting crude product was extracted by means of water/dichloromethane using saturated aqueous sodium bicarbonate solution. After the organic phase was dried by means of Na$_2$SO$_4$ and the extractant removed on a rotary evaporator, the mixture was chromatographed on silica gel (mobile phase ethyl acetate/ n-heptane=3:1). This gave both of the possible diastereomers in the form of colorless crystals:

Unpolar diastereomer: 3.9 g (31%) of melting point 140° C.

$C_{40}H_{45}N_5O_{13}$ (803.8) MS (FAB) 804.1 (M+H$^+$)

mobile phase n-hexane/ethanol=10/1, purity 99.7%, (+)-enantiomer), which was demonstrated with reference to the enantiomer which resulted from the analogous reaction of the polar diastereomer (Example 3d).

$C_{24}H_{25}N_5O_2$ (415.5) MS (FAB) 416.2 (M+H$^+$)

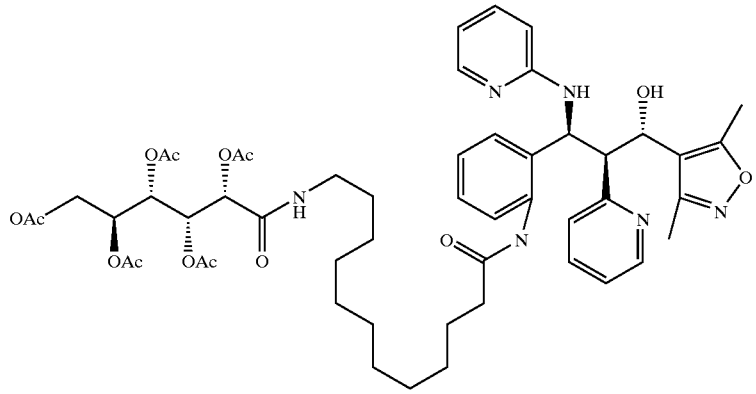

3f

Polar diastereomer: 4.3 g (35%) of melting point 204° C.

$C_{40}H_{45}N_5O_{13}$ (803.8) MS (FAB) 804.1 (M+H$^+$)

1.8 g (4.3 mmol) of the enantiomerically pure compound of Example 3e were reacted with the compound of Example 1j analogously to Example 1k. This gave 3.7 g (86%) of a pale yellow oil.

$C_{51}H_{66}N_6O_{14}$ (987.1) MS (FAB) 987.5 (M+H$^+$)

3g (= Ex. 44 of Table 2)

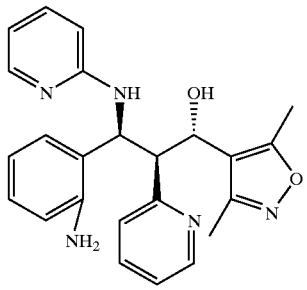

3e (+ Enantiomer)

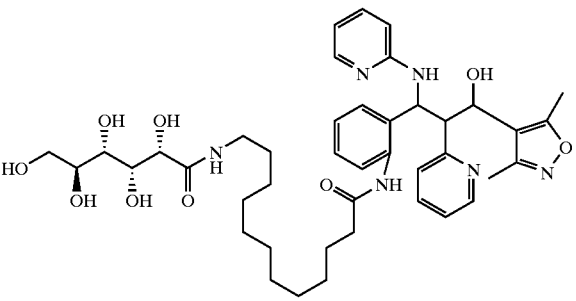

3.5 g (4.4 mmol) of the unpolar diastereomer which was synthesized in Example 3d were reacted as described in Example A1 (reaction time 1 hour; the reaction product is shown in Table 2 as Example 58). The crude product obtained after concentration was dissolved in 80 ml of 0.5M methanolic HCl and the solution was stirred for six hours at room temperature. It was subsequently concentrated under reduced pressure and extracted with CH$_2$Cl$_2$/water. The organic phase was dried by means of Na$_2$SO$_4$ and concentrated under reduced pressure. This gave 1.8 g (98%) of colorless crystals. The compound was present in enantiomerically pure form (column CSP-Chiralpak AD, 250×4.6, 3.7 g (3.8 mmol) of the acetyl compound of Example 3f were deacylated as described in Example A1 (reaction time 2 hours) and worked up. After chromatography on silica gel (mobile phase CH$_2$Cl$_2$/methanol/NH$_3$(33%)=30/10/3), 1.78 g (60%) of colorless crystals of melting point 60° C. were obtained.

$C_{41}H_{56}N_6O_9$ (776.9) MS (FAB) 777.4 (M+H$^+$)

We claim:

1. A combination, comprising at least one compound of formula I

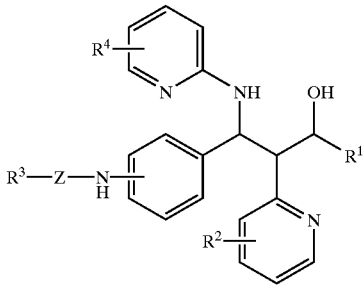

wherein:

R¹ is phenyl or heteroaryl, wherein the aromatic or heteroaromatic ring is unsubstituted, or is mono- to trisubstituted by fluorine, chlorine, bromine, iodine, —OH, —CF$_3$, —NO$_2$, —CN, —(C$_1$-C$_8$)-alkoxy, —(C$_1$-C$_8$)-alkyl, —NH$_2$, —NH—R$^9$, —N(R$^9$)R$^{10}$, —CHO, —COOH, —COOR$^{11}$, —(C=O)—R$^{12}$, —(C$_1$-C$_6$)-alkyl-OH, —(C$_1$-C$_6$)-alkyl(—OH)-phenyl, —(C$_1$-C$_6$)-alkyl-CF$_3$, —(C$_1$-C$_6$)-alkyl-NO$_2$, —(C$_1$-C$_6$)-alkyl-CN, —(C$_1$-C$_6$)-alkyl-NH$_2$, —(C$_1$-C$_6$)-alkyl-NR—R$^9$, —(C$_1$-C$_6$)-alkyl-N(R$^9$)R$^{10}$, —(C$_1$-C$_6$)-alkyl-CHO, —(C$_1$-C$_6$)-alkyl-COOH, —(C$_1$-C$_6$)-alkyl-COOR$^{11}$, —(C$_1$-C$_6$)-alkyl-(C=O)—R$^{12}$, —O—(C$_1$-C$_6$)-alkyl-OH, —O—O—(C$_1$-C$_6$)-alkyl-CF$_3$, —O—(C$_1$-C$_6$)-alkyl-NO$_2$, —O—(C$_1$-C$_6$)-alkyl-CN, —O—(C$_1$-C$_6$)-alkyl-NH$_2$, —O—(C$_1$-C$_6$)-alkyl-NH—R$^9$, —O—(C$_1$-C$_6$)-alkyl-N(R$^9$)R$^{10}$, —O—(C$_1$-C$_6$)-alkyl-CHO, —O—(C$_1$-C$_6$)-alkyl-COOH, —O—(C$_1$-C$_6$)-alkyl-COOR$^{11}$, —O—(C$_1$-C$_6$)-alkyl-(C=O)—R$^{12}$, —N—SO$_3$H, —SO$_2$—CH$_3$, —O—(C$_1$-C$_6$)-alkyl-O—(C$_1$-C$_6$)-alkyl-phenyl, —(C$_1$-C$_6$)-alkylthio, or pyridyl, wherein one or more hydrogen(s) in the alkyl radicals is optionally replaced by fluorine, and wherein phenyl and pyridyl are unsubstiuted or monosubstituted by methyl, methoxy, or halogen;

R² is H, —OH, —CH$_2$OH, —OMe, CHO, or —NH$_2$;

R³ is a sugar residue, disugar residue, trisugar residue, tetrasugar residue, wherein the sugar residue, disugar residue, trisugar residue or tetrasugar residue is unsubstituted or is mono- or polysubstituted by a sugar protective group, HO—SO$_2$, or (HO)$_2$—PO;

R⁴ is H, methyl, F, or —OMe;

R⁹ to R$^{12}$ each independently of one another is H or —(C$_1$-C$_8$)-alkyl;

Z is —NH—(C$_0$-C$_{16}$)-alkyl-C=O—, —O—(C$_0$-C$_{16}$)-alkyl-C=O—, —(C=O)$_m$—(C$_1$-C$_{16}$)-alkyl-(C=O)$_n$, an amino acid residue, a diamino acid residue, wherein the amino acid residue or diamino acid residue is unsubstituted, or mono- or polysubstituted by an amino acid protective group, or a covalent bond;

n is 0 or 1;

m is 0 or 1; or a pharmaceutically tolerated salt, or a physiologically functional derivative thereof, and at least one statin.

2. A pharmaceutical composition, comprising the combination as claimed in claim 1 and a pharmacologically tolerated excipient.

3. The pharmaceutical composition of claim 2, further comprising at least one hypolipidemic active substance.

4. A method for preventing gallstones, comprising administering to a patient in need thereof an effective amount of the combination as claimed in claim 1.

5. A method for treating gallstones, comprising administering to a patient in need thereof an effective amount of the combination as claimed in claim 1.

6. A method for treating hyperlipidemia, comprising administering to a patient in need thereof an effective amount of the combination as claimed in claim 1.

7. A method for preventing gallstones, comprising administering to a patient in need thereof an effective amount of the combination as claimed in claim 1 and at least one further hypolipidemic active substance.

8. A method for treating gallstones, comprising administering to a patient in need thereof an effective amount of the combination as claimed in claim 1 and at least one further hypolipidemic active substance.

9. A method for treating hyperlipidemia, comprising administering to a patient in need thereof an effective amount of the combination as claimed in claim 1 and at least one further hypolipidemic active substance.

10. A combination of claim 1, wherein said at least one statin comprises simvastatin, fluvastatin, pravastatin, cerivastatin, lovastatin, or atorvastatin.

11. A pharmaceutical composition, comprising the combination as claimed in claim 10 and a pharmacologically tolerated excipient.

12. The pharmaceutical composition of claim 11, further comprising at least one hypolipidemic active substance.

13. A method for preventing gallstones, comprising administering to a patient in need thereof an effective amount of the combination as claimed in claim 10.

14. A method for treating gallstones, comprising administering to a patient in need thereof an effective amount of the combination as claimed in claim 10.

15. A method for treating hyperlipidemia, comprising administering to a patient in need thereof an effective amount of the combination as claimed in claim 10.

16. A method for preventing gallstones, comprising administering to a patient in need thereof an effective amount of the combination as claimed in claim 10 and at least one further hypolipidemic active substance.

17. A method for treating gallstones, comprising administering to a patient in need thereof an effective amount of the combination as claimed in claim 10 and at least one further hypolipidemic active substance.

18. A method for treating hyperlipidemia, comprising administering to a patient in need thereof an effective amount of the combination as claimed in claim 10 and at least one further hypolipidemic active substance.

19. A combination, comprising at least one compound of formula I

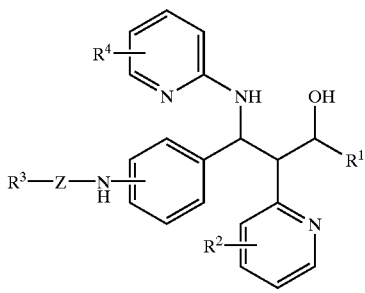

wherein:

$R^1$ is phenyl or heteroaryl, wherein the aromatic or heteroaromatic ring is unsubstituted, or is mono- to trisubstituted by fluorine, chlorine, bromine, iodine, —OH, —$CF_3$, —$NO_2$, —CN, —($C_1$-$C_8$)-alkoxy, —($C_1$-$C_8$)-alkyl, —$NH_2$, —NH—$R^9$, —N($R^9$)$R^{10}$, —CHO, —COOH, —COOR$^{11}$, —(C=O)—$R^{12}$, —($C_1$-$C_6$)-alkyl-OH, —($C_1$-$C_6$)-alkyl(—OH)-phenyl, —($C_1$-$C_6$)-alkyl-$CF_3$, —($C_1$-$C_6$)-alkyl-$NO_2$, —($C_1$-$C_6$)-alkyl-CN, —($C_1$-$C_6$)-alkyl-$NH_2$, —($C_1$-$C_6$)-alkyl-NH—$R^9$, —($C_1$-$C_6$)-alkyl-N($R^9$)$R^{10}$, —($C_1$-$C_6$)-alkyl-CHO, —($C_1$-$C_6$)-alkyl-COOH, —($C_1$-$C_6$)-alkyl-COOR$^{11}$, —($C_1$-$C_6$)-alkyl-(C=O)—$R^{12}$, —O—($C_1$-$C_6$)-alkyl-OH, —O—($C_1$-$C_6$)-alkyl-$CF_3$, —O—($C_1$-$C_6$)-alkyl-$NO_2$, —O—($C_1$-$C_6$)-alkyl-CN, —O—($C_1$-$C_6$)-alkyl-$NH_2$, —O—($C_1$-$C_6$)-alkyl-NH—$R^9$, —O—($C_1$-$C_6$)-alkyl-N($R^9$)$R^{10}$, —O—($C_1$-$C_6$)-alkyl-CHO, —O—($C_1$-$C_6$)-alkyl-COOH, —O—($C_1$-$C_6$)-alkyl-COOR$^{11}$, —O—($C_1$-$C_6$)-alkyl-(C=O)—$R^{12}$, —N—$SO_3$H, —$SO_2$—$CH_3$, —O—($C_1$-$C_6$)-alkyl-O—($C_1$-$C_6$)-alkyl-phenyl, —($C_1$-$C_6$)-alkylthio, or pyridyl, wherein one or more hydrogen(s) in the alkyl radicals is optionally replaced by fluorine, and wherein phenyl and pyridyl are unsubstiuted or monosubstituted by methyl, methoxy, or halogen;

$R^2$ is H, —OH, —$CH_2$OH, —OMe, CHO, or —$NH_2$;

$R^3$ is a sugar residue, disugar residue, trisugar residue, tetrasugar residue, wherein the sugar residue, disugar residue, trisugar residue or tetrasugar residue is unsubstituted or is mono- or polysubstituted by a sugar protective group, HO—$SO_2$, or (HO)$_2$—PO;

$R^4$ is H, methyl, F, or —OMe;

$R^9$ to $R^{12}$ each independently of one another is H or —($C_1$-$C_8$)-alkyl;

Z is —NH—($C_0$-$C_{16}$)-alkyl-C=O—, —O—($C_0$-$C_{16}$)-alkyl-C=O—, —(C=O)$_m$—($C_1$-$C_6$)-alkyl-(C=O)$_n$, an amino acid residue, a diamino acid residue, wherein the amino acid residue or diamino acid residue is unsubstituted, or mono- or polysubstituted by an amino acid protective group, or a covalent bond;

n is 0 or 1;

m is 0 or 1;

or a pharmaceutically tolerated salt, or a physiologically functional derivative thereof, and pravastatin.

20. A pharmaceutical composition, comprising the combination as claimed in claim 19 and a pharmacologically tolerated excipient.

21. A combination, comprising at least one compound of formula I

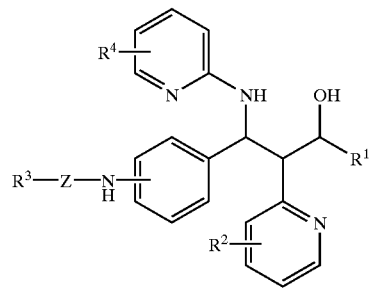

wherein:

$R^1$ is phenyl or heteroaryl, wherein the aromatic or heteroaromatic ring is unsubstituted, or is mono- to trisubstituted by fluorine, chlorine, bromine, iodine, —OH, —$CF_3$, —$NO_2$, —CN, —($C_1$-$C_8$)-alkoxy, —($C_1$-$C_8$)-alkyl, —$NH_2$, —NH—$R^9$, —N($R^9$)$R^{10}$, —CHO, —COOH, —COOR$^{11}$, —(C=O)—$R^{12}$, —($C_1$-$C_6$)-alkyl-OH, —($C_1$-$C_6$)-alkyl(—OH)-phenyl, —($C_1$-$C_6$)-alkyl-$CF_3$, —($C_1$-$C_6$)-alkyl-$NO_2$, —($C_1$-$C_6$)-alkyl-CN, —($C_1$-$C_6$)-alkyl-$NH_2$, —($C_1$-$C_6$)-alkyl-NH—$R^9$, —($C_1$-$C_6$)-alkyl-N($R^9$)$R^{10}$, —($C_1$-$C_6$)-alkyl-CHO, —($C_1$-$C_6$)-alkyl-COOH, —($C_1$-$C_6$)-alkyl-COOR$^{11}$, —($C_1$-$C_6$)-alkyl-(C=O)—$R^{12}$, —O—($C_1$-$C_6$)-alkyl-OH; —O—($C_1$-$C_6$)-alkyl-$CF_3$, —O—($C_1$-$C_6$)-alkyl-$NO_2$, —O—($C_1$-$C_6$)-alkyl-CN, —O—($C_1$-$C_6$)-alkyl-$NH_2$, —O—($C_1$-$C_6$)-alkyl-NH—$R^9$, —O—($C^1$-$C_6$)-alkyl-N($R^9$)$R^{10}$, —O—($C_1$-$C_6$)-alkyl-CHO, —O—($C_1$-$C_6$)-alkyl-COOH, —O—($C_1$-$C_6$)-alkyl-COOR$^{11}$, —O—($C_1$-$C_6$)-alkyl-(C=O)—$R^{12}$, —N—$SO_3$H, —$SO_2$—$CH_3$, —O—($C_1$-$C_6$)-alkyl-O—($C_1$-$C_6$)-alkyl-phenyl, —($C_1$-$C_6$)-alkylthio, or pyridyl, wherein one or more hydrogen(s) in the alkyl radicals is optionally replaced by fluorine, and wherein phenyl and pyridyl are unsubstiuted or monosubstituted by methyl, methoxy, or halogen;

$R^2$ is H, —OH, —$CH_2$OH, —OMe, CHO, or —$NH_2$;

$R^3$ is a sugar residue, disugar residue, trisugar residue, tetrasugar residue, wherein the sugar residue, disugar residue, trisugar residue or tetrasugar residue is unsubstituted or is mono- or polysubstituted by a sugar protective group, HO—$SO_2$, or (HO)$_2$—PO;

$R^4$ is H, methyl, F, or —OMe;

$R^9$ to $R^{12}$ each independently of one another is H or —($C_1$-$C_8$)-alkyl;

Z is —NH-($C_0$-$C_{16}$)-alkyl-C=O—, —O—($C_0$-$C_{16}$)-alkyl-C=O—, —(C=O)$_m$—($C_1$-$C_{16}$)-alkyl-(C=O)$_n$, an amino acid residue, a diamino acid residue, wherein the amino acid residue or diamino acid residue is unsubstituted, or mono- or polysubstituted by an amino acid protective group, or a covalent bond;

n is 0 or 1;

m is 0 or 1;

or a pharmaceutically tolerated salt, or a physiologically functional derivative thereof, and atorvastatin.

22. A pharmaceutical composition, comprising the combination as claimed in claim 21 and a pharmacologically tolerated excipient.

* * * * *

UNITED STATES PATENT AND TRADEMARK OFFICE
CERTIFICATE OF CORRECTION

PATENT NO. : 6,569,835 B2
DATED : May 27, 2003
INVENTOR(S) : Wendelin Frick et al.

It is certified that error appears in the above-identified patent and that said Letters Patent is hereby corrected as shown below:

Title page,
Item [54], Title, after "PREPARATION", insert a comma.

Column 29,
Line 33, "-$(C_1-C_6)$-alkyl-NR-$R^9$," should read -- -$(C_1-C_6)$-alkyl-NH-$R^9$, --.
Lines 37-38, "-O-O$(C_1-C_6)$-alkyl-$CF_3$," should read -- -O$(C_1-C_6)$-alkyl-$CF_3$, --.
Line 39, "-$(C_1-C_6)$-alkyl-$NH_2$," should read -- -O-$(C_1-C_6)$-alkyl-$NH_2$, --.
Lines 48-49, "unsubstiuted" should read -- unsubstituted --.

Column 31,
Line 42, "unsubstiuted" should read -- unsubstituted --.
Line 55, "-$(C=O)_m$-$(C_1-C_6)$-alkyl-$(C=O)_n$," should read
-- -$(C=O)_m$-$(C_1-C_{16})$-alkyl-$(C=O)_n$, --.

Column 32,
Line 30, after "O-$(C_1-C_6)$-alkyl-OH" delete the semicolon and insert a comma.
Line 33, "O-$(C^1-C_6)$-alkyl-N$(R^9)R^{10}$," should read -- -O-$(C_1-C_6)$-alkyl-N$(R^9)R^{10}$, --.
Line 40, "unsubstiuted" should read -- unsubstituted --.

Signed and Sealed this

Twenty-eighth Day of September, 2004

JON W. DUDAS
*Director of the United States Patent and Trademark Office*